United States Patent [19]

Brugnoli

[11] Patent Number: 4,631,966
[45] Date of Patent: Dec. 30, 1986

[54] DEVICE FOR THE SAMPLING AND MEASURING OF THE CONCENTRATIONS OF EXPIRED GASES

[76] Inventor: Siro Brugnoli, Via Valdieri, 31, 00135 Roma, Italy

[21] Appl. No.: 733,434

[22] Filed: May 13, 1985

[30] Foreign Application Priority Data

Apr. 1, 1985 [EP] European Pat. Off. ........ 85830080.9

[51] Int. Cl.$^4$ ............................................. G01N 1/14
[52] U.S. Cl. ............................ 73/863.03; 128/204.22
[58] Field of Search ................ 73/863.03; 128/204.22, 128/719; 73/23

[56] References Cited

U.S. PATENT DOCUMENTS

| | | | |
|---|---|---|---|
| 2,982,131 | 5/1961 | Rosinski | 73/863.03 |
| 3,850,036 | 11/1974 | Sanctuary et al. | 73/863.03 X |
| 4,091,675 | 5/1978 | Jennison | 73/863.03 |
| 4,269,059 | 5/1981 | Baker | 73/863.03 |

*Primary Examiner*—Jerry W. Myracle
*Attorney, Agent, or Firm*—Beveridge, DeGrandi & Weilacher

[57] ABSTRACT

A device for the sampling and measuring of the concentrations of the gases expired by a person, comprising a "mediator" whose functioning may be overlapped, for what concerns the results, to the one that could be obtained by varying the capacity of a dynamic chamber, being (K)-times bigger, where ($K=F/Fc$), with (F) being the flow of the gas to be analyzed and (Fc) being the sampling flow. The sampling pump (4) is always in phase with the ventilation signal, and the capacity is always directly proportional to said ventilation according to a factor determined by amplifier (6) at variable gain and by power amplifier (5). When the ventilation signal increases, an integrator circuit (7) controls the gain of stage (6). This allows to vary the proportionality factor between ventilation and sampling flow of the pump. In this way the air volume passing through the mixing chamber (2) will be practically constant, and a functioning will be obtained being equivalent to the one of a dynamic chamber.

5 Claims, 3 Drawing Figures

DEVICE FOR THE SAMPLING AND MEASURING OF THE CONCENTRATIONS OF EXPIRED GASES

The present invention concerns a device for the sampling and measuring of the concentrations of the gases expired by a person by means of a capacity meter, with a rectifier that allows the sampling of only those gases passing in one of the possible directions.

It is already well known that the analysis of a gas mixture may be performed by means of different methods, according to the instruments available and the purpose of measuring.

If, e.g., momentary measures are to be obtained, it is necessary to make use of a gas sampling system and of an analysis instrument with a very short response time. On the contrary, if only the average value of the concentration of a determined gas is to be obtained, it is easier to collect all the gas in a bag.

In this second case the bag has the function of a "mechanical mediator" and this is why it is called "mixing chamber". The analysis of the gas may be performed with a QUICK as well as with a SLOW analyzer.

The measuring becomes more complicated when the time variation of the average concentration is to be monitorized.

In fact, in this case the phase displacement, existing between the gas volume and the measure of the average concentration, should be considered. In fact, apart from the constant response time of the gas analyzer, a further variable term exists, due to the washing time of the mixing chamber.

This is strongly linked to the passing speed (ventilation) of the gas inside the chamber, and it results to be as much shorter as higher the ventilation is.

If an instrument with a short response time is chosen, the monitorizing may be effected by aligning the ventilation signal with the concentration signal, according to said ventilation. However, this solution makes a periodic concentration measuring impossible, because the response of the measuring system varies according to the ventilation.

If, on the contrary, a slow instrument will be used, it is obvious that it won't be possible to overcome that ventilation value to which corresponds such a quick washing of the chamber that the instrument won't be able any longer to take the measure.

In this case, the only solution is shown by the capacity variations of the chamber according to the ventilation.

Obviously, this means that a mechanical system will be used, realizing the so-called "dynamic mixing chamber". If by T the turnover of the chamber is shown, said turnover being in turn shown by the number of the washings effected in one minute, the chamber's capacity will have to respect the following relation:

$$Tmin \times C < VE < Tmax \times C, \qquad (R)$$

where VE is the ventilation in one minute, Tmin is the minimum turnover number for guaranteeing the chamber's renewal, Tmax is the maximum turnover number linked to the analyzer's response speed, and C is the chamber's capacity.

The relation R is valid of the whole volume of VE passes inside the mixing chamber.

When, however, a volume sampling is realized, VE will be replaced by the gas quantity passing, in one minute through the chamber.

As the sampling flow Fc is proportional to the one F of the gas to be analyzed, according to a proportionality factor—that will be shown with K—, the relation will be rewritten as follows:

$$Tmin \times C < VE/K < Tmax \times C, \qquad (R1)$$

where $K = F/Fc$.

Once the turnover variation range (Tmin÷Tmax) has been fixed according to the analyzer's response time and the mediator time constant (shown by the mixing chamber), the value of C depends on the proportionality factor K.

As can be seen, once the values of the variants K, T and C are fixed, one limitation is left to be removed on the ventilation.

In fact, said ventilation may not vary beyond a range Tmin÷Tmax. As it has already been underlined, when VE goes out of this range, it will be necessary to vary the value of the mixing chamber's capacity, so that the relation R1 will always be true.

The device according to the present invention solves the problem by varying the value of K instead of the one of C.

The relation R1 may therefore be written as follows:

$$VEmin = Tmin \times C \times K; \; VEmax = Tmax \times C \times K. \qquad (R2)$$

It is obvious that for any value of ventilation VE, there is always a value K that satisfies the relation R2, and to which correspond two new values of VEmin and VEmax.

According to this situation, a "mediator" is realized whose functioning may be overlapped—for what concerns the results—to the one that could be obtained varying the capacity of a dynamic chamber being K-times bigger.

The device according to the present invention is provided with an electronic circuit performing the control of the proportionality factor K according to ventilation VE.

Said circuit consists in an amplifier whose inlet signal consists in the flow of gas to be analyzed, and the outlet thereof operates the sampling pump.

The amplification factor K is controlled by an electronic integrator, the time constant thereof being variable according to the measuring to be performed.

Said device practically "pursues" the ventilation variations controlling the value of K, in such a way that the turnover always remains in the range of Tmin÷Tmax.

The value of the time constant shows the time necessary for performing the variation of K.

At this point it should be underlined that is is not necessary to "pursue" the ventilation in a real time because for each value of K the same may vary between a minimum and a maximum as shown by the relation R2.

The same control that is performed by the device according to the present invention by means of an analogic circuit, may of course be performed by a microcomputer or by a digital device.

The main feature of the present invention consists in the possibility of always measuring the average concentration value, independently from the ventilation, without making use of the variable capacity chamber nor of the variable alignment of the ventilation and concentration signals.

The present invention may be applied to all instruments for the measuring of the partial volume of a gas in a gaseous mixture, because the system's outlet represents the concentration value, which if multiplied by the ventilation value, gives the partial volume of the gas being examined.

If the control of the sampling pump is effected by means of a microcomputer, it is possible to measure not only the average concentration value, but also the relative value at an exact ventilation phase, like e.g. the end of an expiration.

This will be obtained by simply disengaging the pump during those phases that do not undergo any measuring.

The present invention will be now described more in detail according to the attached drawings showing a preferred embodiment thereof.

Figure 1:
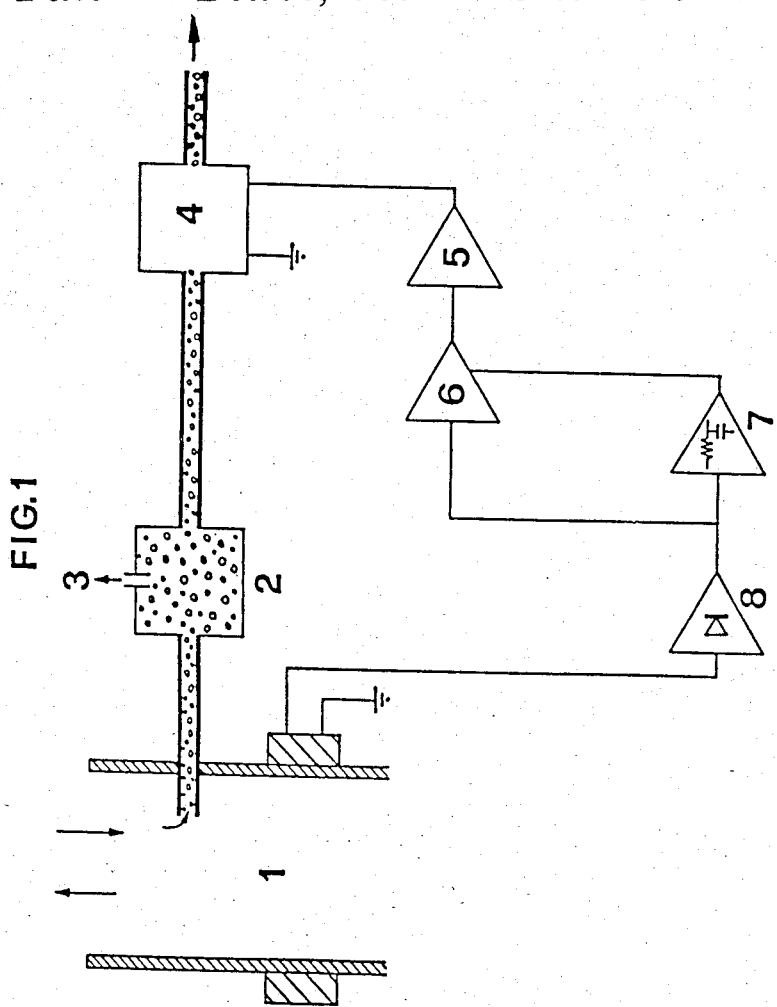
FIG. 1 shows a scheme of the device according to the present invention, connected to a capacity meter.

The figures show a device for the sampling and measuring of expired gases which pass through the capacity meter 1 with the rectifier 8 that allows the sampling of only those gases passing in one of the two possible directions.

This is of particular importance, should the present invention be applied in the medical field for exploring, e.g., the composition of the gases expired by a person.

The sampling pump is always in phase with the ventilation signal, and the capacity is always directly proportional to said ventilation, according to a factor determined by amplifier 6 at variable gain and by power amplifier 5.

When the ventilation signal increases, an integrator circuit 7 controls the gain of stage 6. This allows to vary the proportionality factor between the ventilation and the sampling flow of the pump.

In this way, the air volume passing through mixing chamber 2 will be constant in time and a functioning will be obtained equivalent to the one of a dynamic chamber. The sampling gas will be drawn at outlet 3 of microchamber 2.

The time constant of integrator 7, as already said, may be varied according to the kind of measuring that is to be obtained.

Practically, this is an index of the speed at which the sampling system "pursues" the ventilation variations.

Figure 2:
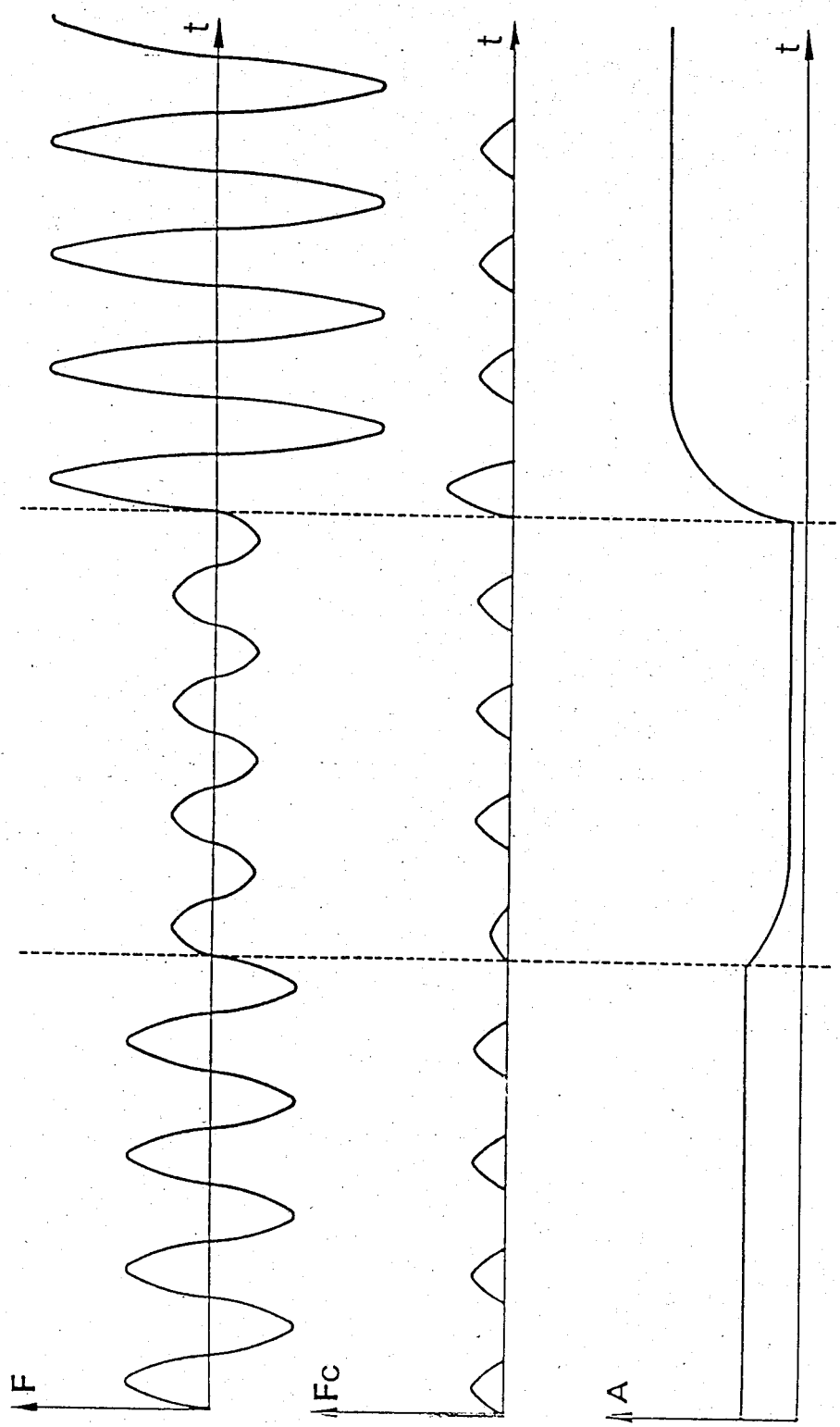
FIG. 2 shows the temporary diagrams of the outlet of the survey system of the flow F, of the flow sampling pump Fc and outlet A of the integrator.

For what concerns the diagrams of FIG. 2, the first Ft shows a hypothetic capacity signal F, obtained by means of detector 1.

In the second diagram Fc, T shows the corresponding sampling flow of pump 4. It will be noted that the shape of the wave of Fc is similar to and in phase with the one of F in the positive half-period relating, e.g., to the expirating phase, while it is annulled in the negative half-period of F relating, e.g., to the inhaling phase.

The proportionality factor F/Fc is determined by stages 5, 6. When the ventilation decreases, the sampling flow Fc is always similar to the one of F but, with a time proportional to the own time constant, the integrator lowers the outlet level thereof, as shown in diagram A, t.

As the integrator's outlet performs an automatic gain control on stage 6, the amplification factor of the same increases, so that the sampling pump 4 follows the flow F with a greater proportionality factor than the starting one.

On the contrary, when the ventilation increases, the integrator's outlet signal—also increasing—will lower the outlet of stage 6 so that the sampling flow be brought back to such a level as to allow a nearly constant turnover of the mixing chamber.

Figure 3:
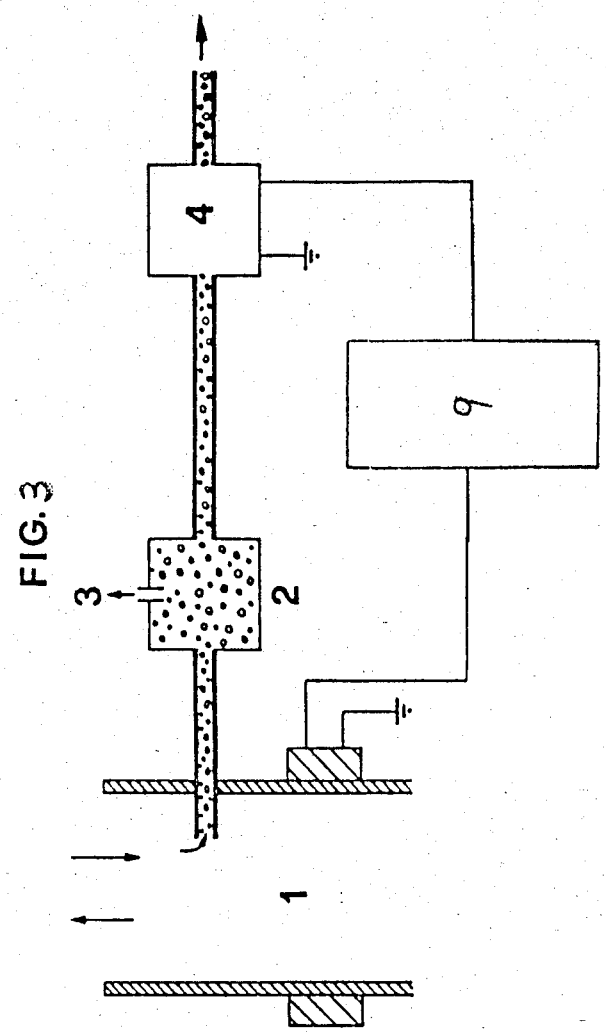
FIG. 3 shows an alternative embodiment of a device according to the present invention, also connected to a capacity meter.

FIG. 3 shows an alternate embodiment of a device in accordance with the present invention wherein control of sampling pump 4 is effected by means of microcomputer 9. Microcomputer 9 can interrupt the operation of pump 4 at any time during receipt of the ventilation signal to allow measurement of the concentration of gases, for example, at this end of an expiration. Thus, it is not only possible to measure the average concentration value, but also a relative value at any time during ventilation.

I claim:

1. A device responsive to a ventilation signal for sampling and measuring gas concentrations in expired gases, said device comprising:

a mixing chamber having inlet means for receiving a flow of the expired gas defined by F(t), first outlet means for venting a sample flow of the expired gas defined by Fc(t), and second outlet means, wherein a proportionality factor K is defined by $K = F(t)/Fc(t)$;

a sampling pump connected to said second outlet means, said pump operating in phase with said ventilation signal to regulate said expired gas flows through said mixing chamber; and control means for controlling said pump, wherein said control means includes a power amplifier, an integrator and a variable gain amplifier connecting said power amplifier and said integrator, said variable gain amplifier providing an electrical signal representative of said proportionality factor K, said factor depending on the gain of said variable amplifier, said integrator receiving said ventilation signal and varying said gain and therefore said proportionality factor whereby said sample flow Fc(t) is substantially constant.

2. A device as claimed in claim 1, wherein when said ventilation signal decreases, said integrator increases said gain of said variable gain amplifier whereby said proportionality factor $K = F/Fc$ is increased.

3. In combination with an analyzer having a maximum response speed, a device as claimed in claim 1, wherein said mixing chamber has a minimum turnover number defined by Tmin and a maximum turnover number defined by Tmax dependent upon said maximum response speed, said controller controlling said pump to regulate said chamber whereby the turnover of said chamber remains within the range of Tmin and Tmax.

4. A device as claimed in claim 1, wherein said integrator is variable, the time constant of said integrator being variable according to the measurement to be made.

5. A device responsive to a ventilation signal for sampling and measuring gas concentrations in expired gases, said device comprising:

a mixing chamber having inlet means for receiving a flow of expired gas defined by F(t), first outlet means for venting a sample flow of the expired gas defined by Fc(t), and second outlet means, wherein a proportionality factor K is defined by $K=F(t)/Fc(t)$;

a sampling pump connected to said second outlet means, wherein said pump operates in phase with said ventilation signal to regulate said expired gas flows through said mixing chamber; and a microcomputer for controlling said pump, said microcomputer receiving said ventilation signal and varying said proportionality factor K in response thereto, whereby said sample flow Fc(t) is substantially constant, said microcomputer intermittently interrupting operation of said pump for a predetermined time corresponding to a predetermined portion of said ventilation signal.

* * * * *